United States Patent [19]

Grendahl

[11] Patent Number: 4,921,496
[45] Date of Patent: * May 1, 1990

[54] RADIALLY SEGEMENTED ZONE OF FOCUS ARTIFICIAL HYDROGEL LENS

[76] Inventor: Dennis T. Grendahl, 2070 Shoreline Dr., Orono, Minn.

[*] Notice: The portion of the term of this patent subsequent to Jan. 17, 2006 has been disclaimed.

[21] Appl. No.: 258,029

[22] Filed: Oct. 17, 1988

Related U.S. Application Data

[63] Continuation-in-part of Ser. No. 88,249, Aug. 24, 1987, Pat. No. 4,798,609.

[51] Int. Cl.$^5$ ............................................... A61F 2/16
[52] U.S. Cl. ........................................................ 623/6
[58] Field of Search ............................. 623/6; 351/161

[56] References Cited

U.S. PATENT DOCUMENTS

| 4,240,163 | 12/1980 | Galin | 623/6 |
| 4,704,016 | 11/1987 | deCarle | 351/161 |
| 4,731,078 | 3/1988 | Stoy | 623/6 |
| 4,798,609 | 1/1989 | Grvendahl | 623/6 |

FOREIGN PATENT DOCUMENTS

| 0162573 | 11/1985 | European Pat. Off. | 623/6 |
| 8603961 | 7/1986 | PCT Int'l Appl. | 623/6 |
| 2181355 | 4/1987 | United Kingdom | 623/6 |

Primary Examiner—Richard J. Apley
Assistant Examiner—James Prizant
Attorney, Agent, or Firm—Hugh D. Jaeger

[57] ABSTRACT

An implantable or contact hydrogel lens for replacement of a defective natural lens in an eye in which various portions of the lens have different powers and focal lengths to produce in-focus images on different portions of the retina of objects which are located at various distances from the eye, thereby substituting for the natural focusing action of the eye. The image processing capability of the brain functions to largely ignore the out-of-focus images and concentrate on the in-focus image of the object selected by the brain for consideration.

18 Claims, 17 Drawing Sheets

RADIALLY SEGEMENTED ZONE OF FOCUS ARTIFICIAL HYDROGEL LENS

CROSS REFERENCES TO CO-PENDING APPLICATIONS

This application is a Continuation-in-Part of application Ser. No. 07/088,249, filed Aug. 24, 1987, entitled "Radially Segmented Zone of Focus Artificial Lens", now U.S. Pat. No. 4,798,609; which is related in part to application Ser. No. 07/258,019, filed Oct. 17, 1988, entitled "Multiple Element Zone of Focus Artificial Hydrogel Lens", which is a Continuation-in-Part of Application Ser. No. 07/088,412, filed Aug. 24, 1987, Entitled "Multiple Element Zone of Focus Artificial Lens", now U.S. Pat. No. 4,778,462; application Ser. No. 07/258,027, filed Oct. 17, 1988, entitled "Cylindrically Segmented Zone of Focus Artificial Hydrogen Lens", which is a Continuation-in-Part of application Ser. No. 07/088,413, filed Aug. 24, 1987, entitled "Cylindrically Segmented Zone of Focus Artificial Lens", now U.S. Pat. No. 4,795,462; and application Ser. No. 07/258,028, filed Oct. 17, 1988, entitled "Laminated Zone of Focus Artificial Hydrogel Lens", which is a Continuation-in-Part of application Ser. No. 07/088,428, filed Aug. 24, 1987, entitled "Laminated Zone of Focus Artificial Lens", now U.S. Pat. No. 4,798,609.

BACKGROUND OF THE INVENTION

1. Field of the Invention

The present invention pertains to an implantable intraocular lens, and more particularly, pertains to a hydrogel lens containing radially segmented lens elements.

This invention relates to hydrogel lenses which have discrete areas which serve to bring impinging rays to a focus in a specific area of the focal plane. Such lenses are called zone of focus lenses and are particularly useful for implantation into the eye as a substitute for the natural lens since, when in combination with the brain, the lenses effectively replicate the ability of the natural lens to bring objects at varying distances to a sharp focus.

The invention relates specifically to a zone of focus lens in which the hydrogel lens is radially divided into pie-shaped lens elements extending from the lens center. Each element serves to bring the impinging rays from an object at a predetermined distance to a focus on a particular region of the retina. By selecting various powers for the hydrogel lens elements, it is possible to have an object at a given distance brought to an acceptable focus by at least one of such lens elements. In this manner, an in-focus image (sharp image) is created on a particular portion of the retina serviced by that element. It has been found that the processing of the image by the brain results in the selective consideration of the sharpest image and the virtual discard of the other, out-of-focus images created by other segments.

2. Description of the Prior Art

Limited attempts to produce a lens having areas of varying powers have been made. There have been many attempts to produce implantable lenses which serve for both close and far seeing, similar to the bifocal spectacles. In general, such lenses have been produced with two regions having different powers. The light which impinges on the retina passes through one region to the exclusion of the other. In such a system, only one region of the lens is used at a time, and there is no accommodation by the brain to reject an out-of-focus image. Great care and accuracy must be used in the preoperative measurements since both the near and far powers must be accurately determined. Since the near and far powers are not specifically interrelated, the inventory requirements are compounded since a variety of near powers must be available for every far power.

Further, the rigid materials used for lenses have required relatively large incisions for implantation, but the post-operative recovery period is shorter when a small incision is made.

The present invention overcomes the disadvantages of the prior art by providing a hydrogel lens capable of implantation through a small incision, which includes radially segmented lens elements where each lens element or group of lens elements is of a different power.

SUMMARY OF THE INVENTION

The lens is a composite of pie-shaped hydrogel elements, each of which has a distinct power and focal length. Each element brings the impinging rays to bear on a predetermined portion of the retina, which may be either unique to that element or shared with other elements of like power. The hydrogel lens elements are selected to have a sufficient range of powers to accommodate the projected use. That is, the value of the power and the number of elements will be determined by the projected use. Most uses can be accommodated with a lens having two or three powers to accommodate objects at near, far and intermediate distances. These powers can be distributed among a like number of elements or a number of elements which is two, three or even more times the number of powers. The distribution of powers among the elements need not be done equally. For example, if most of the sight is required at close distances, the number of elements for this distance can be increased and the number of elements for far vision correspondingly decreased.

Accommodation of the brain to such an arrangement may be enhanced by adding a distinctive color to the elements of like power. This approach may be utilized where loss or impairment of color vision is of little consequence.

Hydrogel lens elements of differing powers can be provided by grinding or otherwise forming a uniform lens surface over a composite structure of pie-shaped hydrogel elements having differing indices of refraction.

In the alternative, the pie-shaped elements can be fabricated of like hydrogel material and the differing powers obtained by grinding, molding or otherwise shaping the surface of the individual pie-shaped element to provide individual curvatures.

Lens is a generic term for intraocular lens, intracorneal lens, or contact lens. Lenses also include any optical lens such as a camera, television, telescopes, projectors, optical instruments, glasses, etc.

It is a principal object hereof to provide a hydrogel lens incorporating a radially segmented zone of focus lens.

It is therefore an object of this invention to provide a very low cost zone of focus hydrogel lens which will make the replacement of a defective natural lens available to many who cannot now afford the operation.

It is another object of the invention to provide a minimum cost zone of focus hydrogel lens which does not require either an extensive inventory of various powers and combination of powers, or extensive preoperative measurement prior to implantation into the eye as a replacement for a defective lens.

Still another object of this invention is to provide a very low cost approach to the replacement of a defective lens by providing a very nearly universal hydrogel lens which provides vision adequate to allow a normal life style.

These lenses can be used as replacements for the presbyoptic lens of the aging population and thereby allowing for both near and distant vision without the use of spectacles. Intraocular lenses sometimes become decentered. Distant and near vision with this zone of focus lens will not be affected by decentration.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
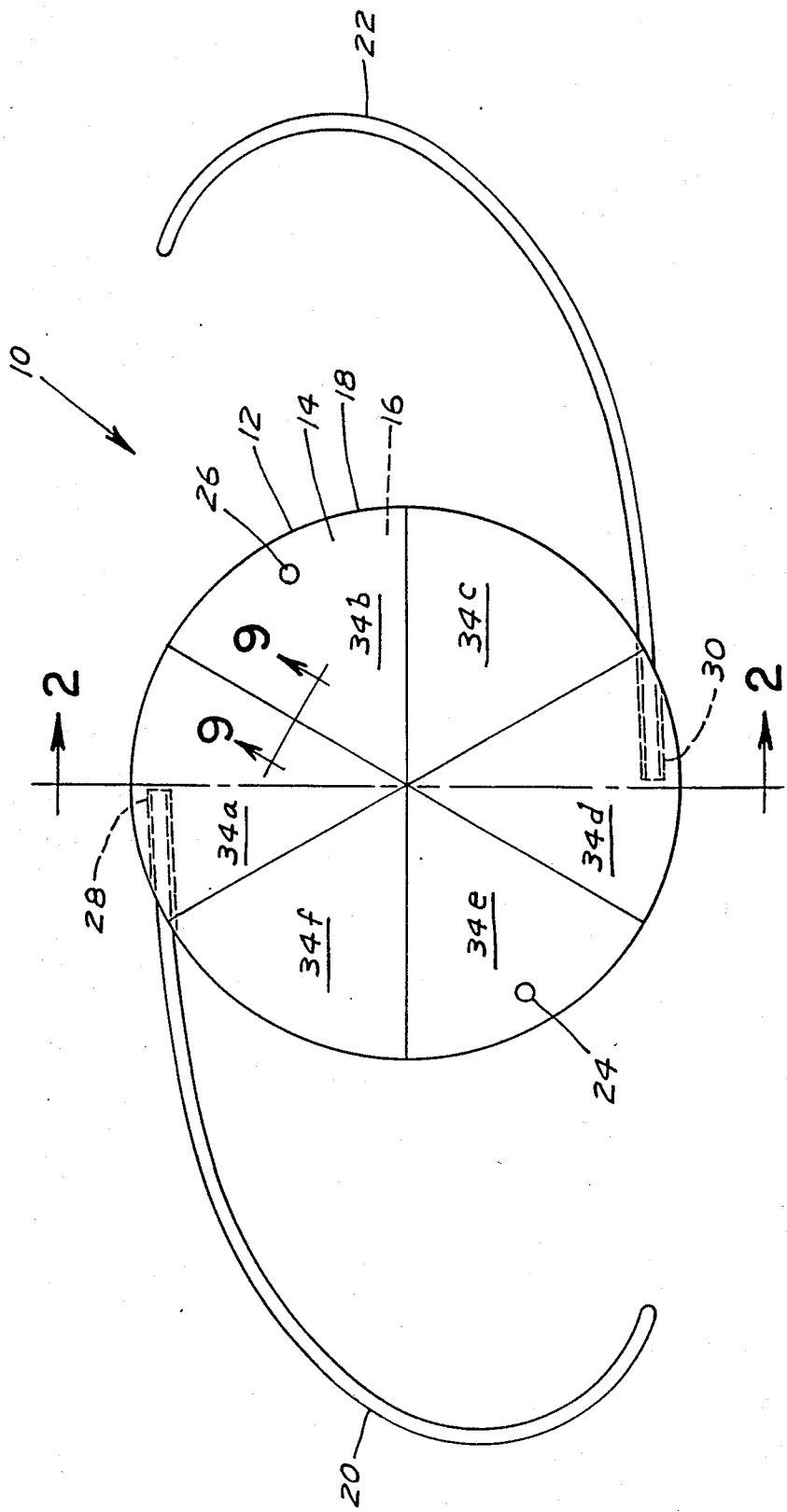
FIG. 1 illustrates a plan VieW of a radially segmented zone of focus hydrogel lens according to the invention.

FIG. 1 illustrates a plan view of a radially segmented zone of focus lens 10, of hydrogel material, which includes an optic 12, a convex anterior surface 14, a plano posterior surface 16, an edge 18 therebetween, open loop haptics 20 and 22 for fixation of the lens to the interior of the eye, and positioning holes 24 and 26. Haptics 20 and 22 secure into holes 28 and 30 by known processes. The shape of lens 10 may be varied to accommodate optical or other requirements. The lens 10 is primarily illustrated as a plano convex lens, but can assume any other convenient shape, such as meniscus, biconvex or any other desired lens shape. Lens 10 has a plurality of pie-shaped lens elements 34a-34f. Each of the elements 34a-34f have distinct focal length (power) so as to bring objects of differing distance into focus in a common focal plane. In general, it will be found that two or three powers will be optimum in terms of performance within the human eye. A greater number of powers may not provide adequate sharp images for consideration by the brain and more unduly complicate the process of adaptation by the patient. With two different powers, the elements of like power can be interspersed with segments of the other power. Alternatively, elements of like power may be located in the regions where adaptation is facilitated. Further alternatives include locating the elements in accordance with physical characteristics of the eye itself to accommodate retinal or corneal defects. While six pie-shaped lens elements 34a-34f are shown in the embodiment of FIG. 1 it will be appreciated that the invention is not so limited, and either a greater or smaller number of elements is permissible. The power of the individual lens elements are determined by their radius of curvature and the index of refraction, either of which may be varied to provide the desired power. In the embodiment of FIG. 1, the radius of curvature for all elements is the same and the index of refraction of the hydrogel material is varied to provide the necessary difference in power. The index of refraction can be modified by changing the length of the polymer while maintaining compatibility with the other characteristics or by the introduction of suitable additives.

Fabrication of lens 10 may begin with the creation of a composite rod or similar structure in which the cross section of the rod resembles the plan view of FIG. 1. Such a rod can be made by simultaneous extrusion of the elements from differing material or by individual extrusion or other shaping and subsequent joining of the elements. While the extrusion process has certain advantages, particularly that of low cost, the individual fabrication of the elements and subsequent joining affords the opportunity to use hydrogel materials with different indices of refraction and to mask the junction with an anti-reflection coating.

In either case, the resulting blank may be sliced and fabricated into lenses either by further molding in a die which has the radii of curvature for the desired optical characteristics, by conventional lathe cutting, or other similar optical finishing techniques.

Figure 2:
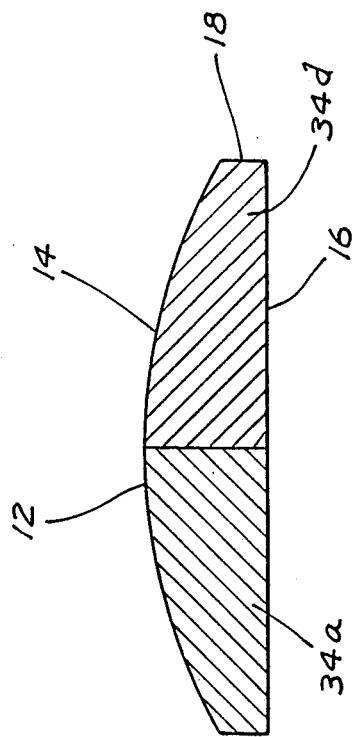
FIG. 2 illustrates a cross-sectional view of an embodiment of the radially segmented zone of focus hydrogel lens taken along line 2—2 of FIG. 1.

FIG. 2 illustrates a cross-sectional view of the radially segmented zone of focus lens taken along line 2—2 of FIG. 1 where all numerals correspond to those elements previously described.

Figure 3A:
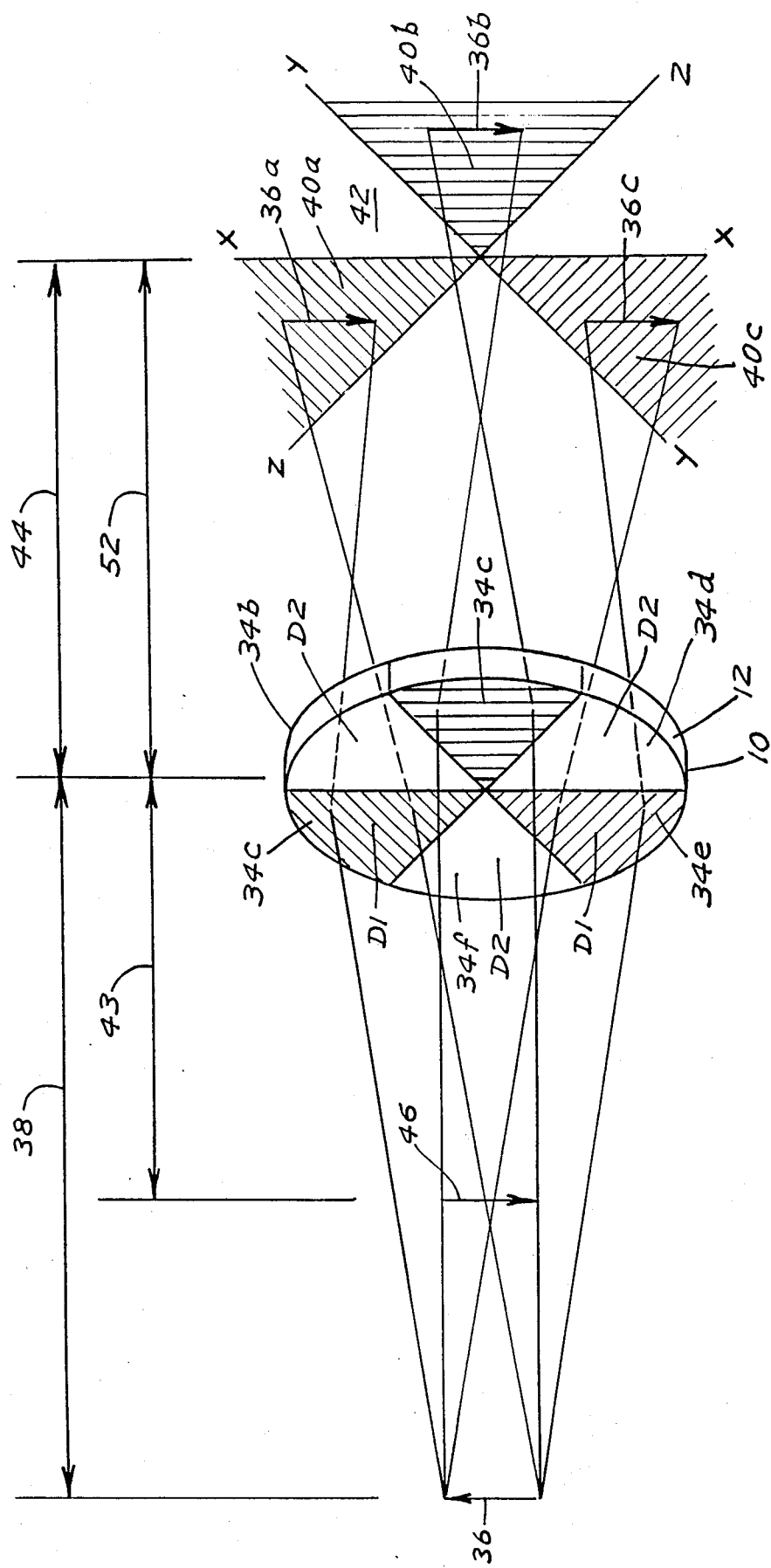
FIGS. 3A and 3B illustrate schematic isometric views of an optical system in which the radially segmented zone of focus hydrogel lens develops individual images for each element.
Figure 3B:
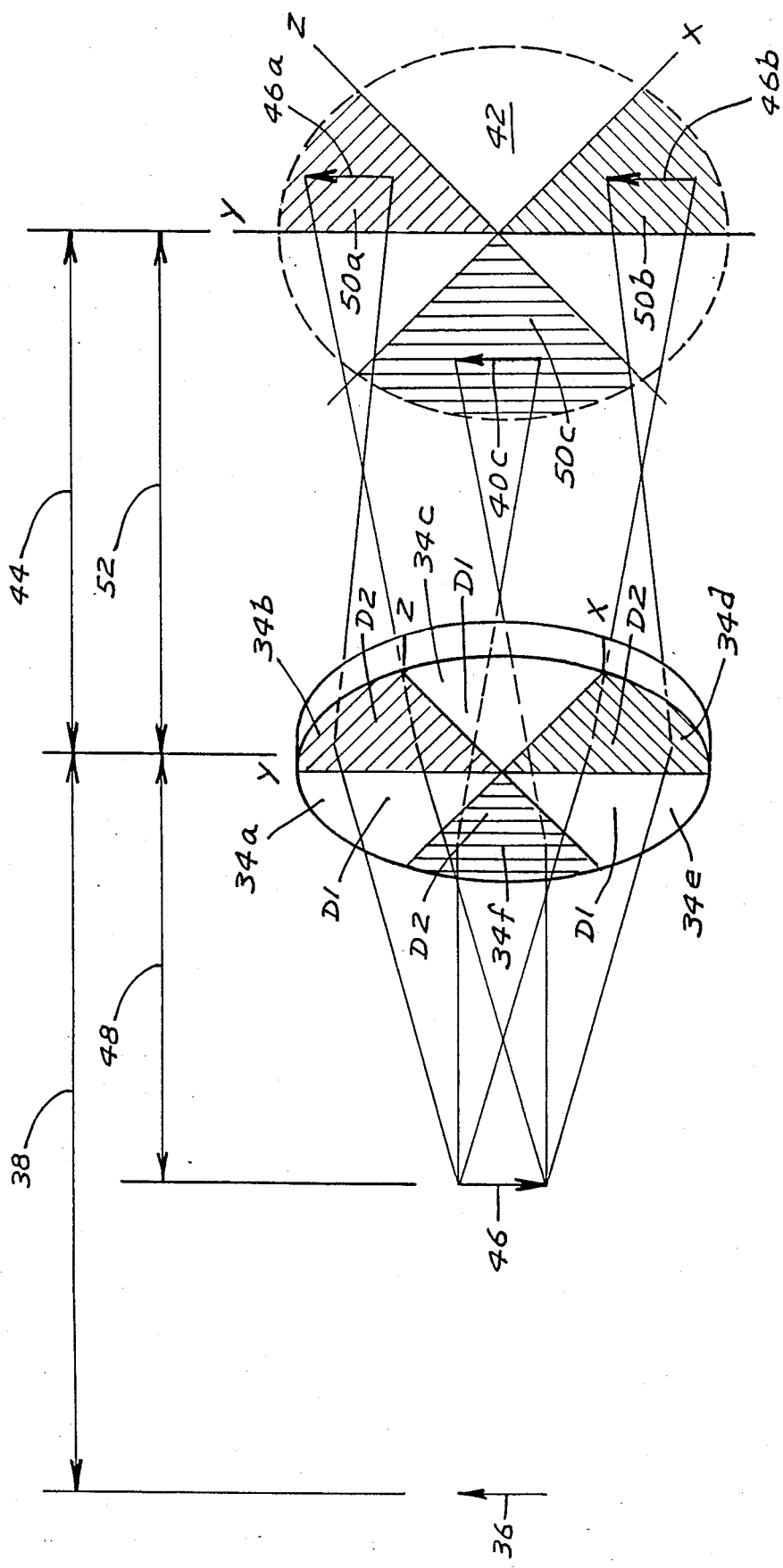

FIGS. 3A and 3B illustrate schematic illustrations of an optical system utilizing the lens of FIG. 1, which incorporates two illustrations for the purpose of clarity. The hydrogel lens 10 has a plurality of lens elements 34a–34f. The lens elements 34a, 34c and 34e have a common power D1 and bring a far object 36 located at a far distance 38 to focus on a focal area 40a–40c and is shown as image 36a–36c each of which lies on a configured focal plane 42 as indicated by an x-y-z plot axis at a far focal distance 44. The distance between the optic 12 and the configured plane 42, terminates at focal plane 42. In FIG. 3 the lens elements 34b, 34d and 34f have a common power D2 and bring a near object 46, located at a near distance 48 to a focus in areas 50a–50c and is shown as images 46a–46c, 46c, each of which is on a focal plane 42 as indicated by an x-y-z axis, at a near focal distance 52 also terminating at the configured plane 42. It can be seen that the lens elements 34a–34f of lens 10 each produce an image in corresponding areas of the focal plane 42 on an area corresponding generally to the shape of the lens elements. For example, element 34a produces a sharp image 36a of far object 36 in the region of the focal plane shown as 40a. Similarly, element 34b produces a sharp image 46a of near object 46 in the area 50a of the focal plane 42.

It will be appreciated that the elements 34b, 34d and 34f, in addition to producing a sharp image of the near object 46, will also produce an out-of-focus image of the far object 36. Similarly, the elements 34a, 34c and 34e will simultaneously produce a sharp image of far object 36 and an out-of-focus image of near object 46. The adaptive power of the brain effectively rejects the out-of-focus image and permits the in-focus image of the desired object to predominate. The adaptive capability varies with individuals and can sometimes be enhanced by selective positioning of the elements in accordance with personal characteristics of the individual.

Figure 4:
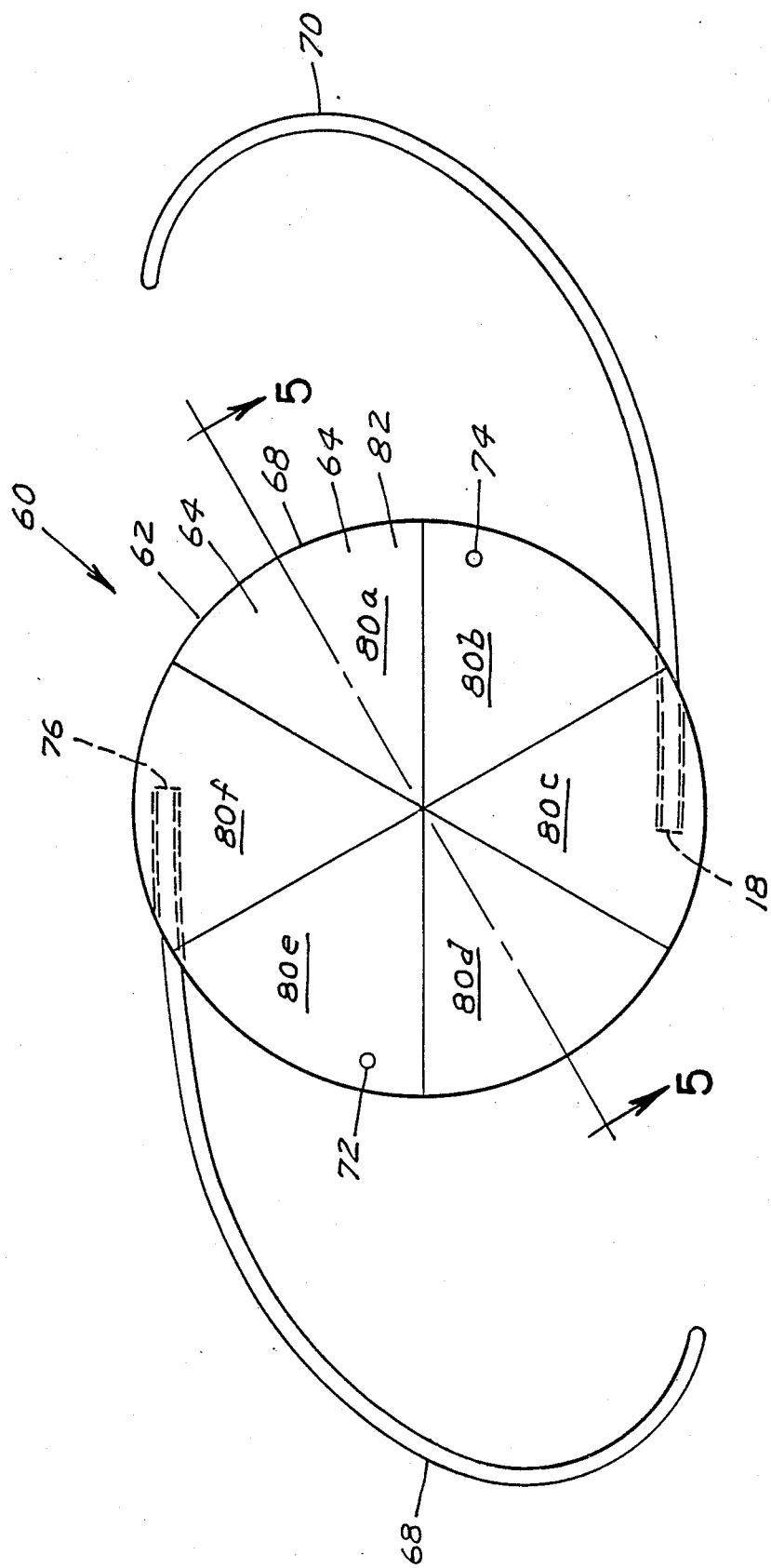
FIG. 4 illustrates a plan view of an embodiment of the radially segmented zone of focus hydrogel lens having a different radius of curvature for the lens elements.

FIG. 4 illustrates a plan view of a radially segmented zone of focus hydrogel lens 60 of PMMA or other suitable material including an optic 62, a convex anterior surface 64, a plano posterior surface 66, an edge 68 therebetween, open loop haptics 68 and 70 for fixation of the lens to the interior of the eye and positioning holes 72 and 74. Haptics 68 and 70 secure into holes 76 and 78. The hydrogel lens 60 is primarily illustrated as a plano-convex lens, but can be biconvex, meniscus or other desired shape. The hydrogel lens 60 is similar in overall design to hydrogel lens 10 of FIG. 1 except the pie-shaped lens elements 80a–80f are made from material having the same index of refraction. The differing powers are provided by fabricating the lens elements with different radii of curvature. Lens elements 80a, 80c and 80e have less curvature than elements 80b, 80d, and 80f, the forms of which represent the lower power of this element. Since the elements do not have a uniform curvature, conventional grinding or lathe cutting techniques are not generally adequate for fabrication. It may be desirable to form the lens in a die having suitable dimensions or to individually fabricate the elements and join them after at least one surface is fabricated.

Since the embodiment shown in FIG. 4 will have at least one discontinuous surface, it may be desirable to provide a smooth layer overcoating 82 on one or more surfaces, to avoid irritation when the lens is implanted.

Figure 5:
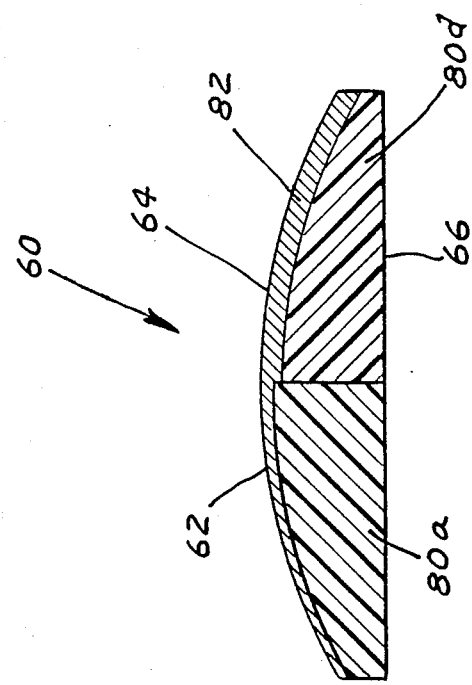
FIG. 5 illustrates a cross-sectional view of the radially segmented zone of focus hydrogel lens taken along line 5—5 of FIG. 4.

FIG. 5 illustrates a cross-sectional view of the lens of FIG. 4 taken along line 5—5 of FIG. 4 where all numerals correspond to those elements previously described. Shown in particular is the difference of curvature of the lens elements. FIGS. 6-8 and FIGS. 9-15 are illustrative of embodiments of lens element arrangements which utilize colored elements to enhance the adaptation of the individual and are of similar and like construction with regard to surfaces, loops, positioning holes and the like, as previously described in previous figures.

Figure 6:
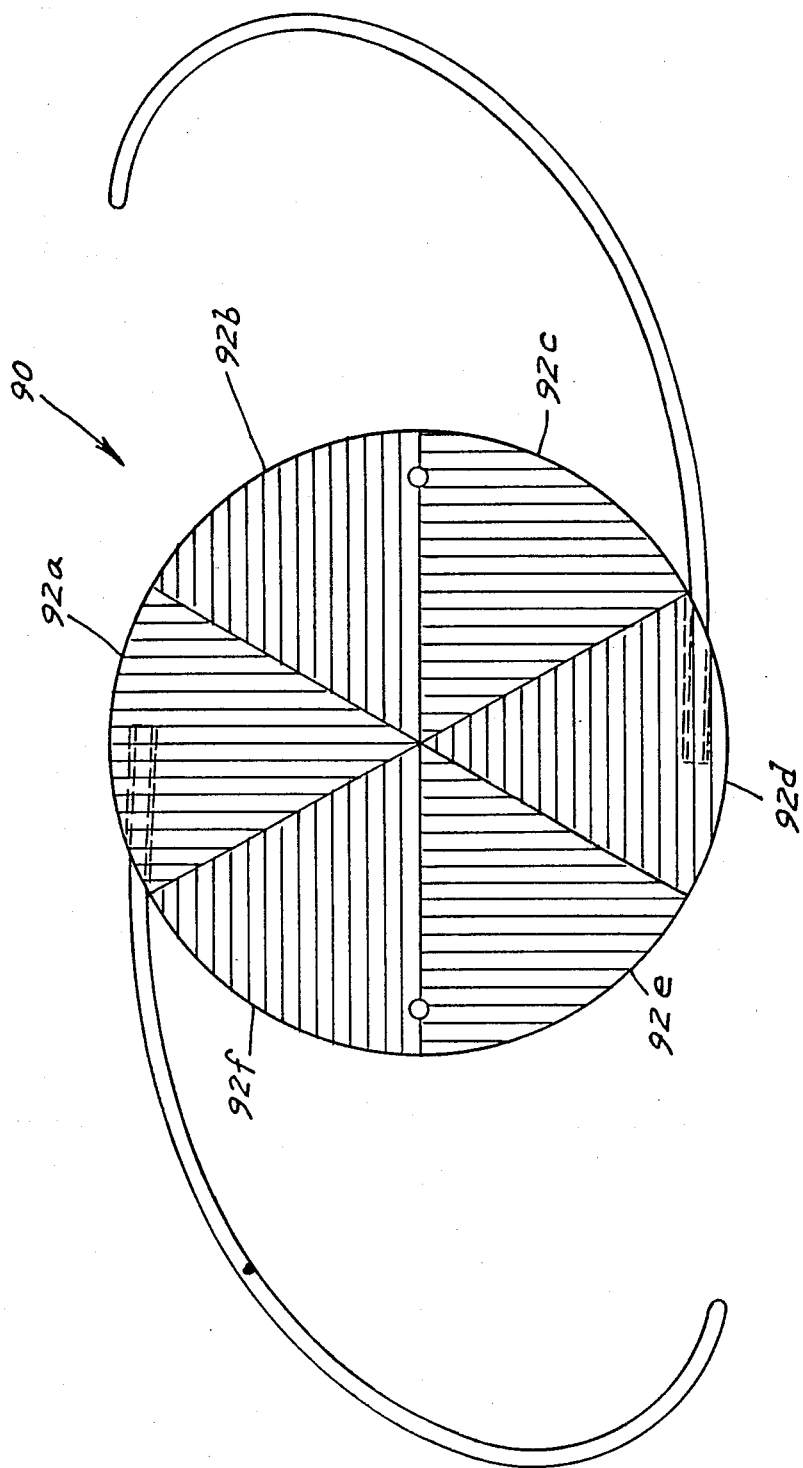
FIG. 6 illustrates a plan view of a radially segmented zone of focus lens in which the hydrogel lens elements are alternating in color.

FIG. 6 illustrates a plan view of a radially segmented zone of focus lens in which the lens elements 92a, 92c and 92e of lens 90 have like powers and are colored red or some other suitable color. Lens elements 92b, 92d and 92f have like powers, differing from the common power of lens elements 92a, 92c and 92e, and are of a different suitable color such as blue. The colors assist the brain in distinguishing the images produced from the two groups of elements.

Figure 7:
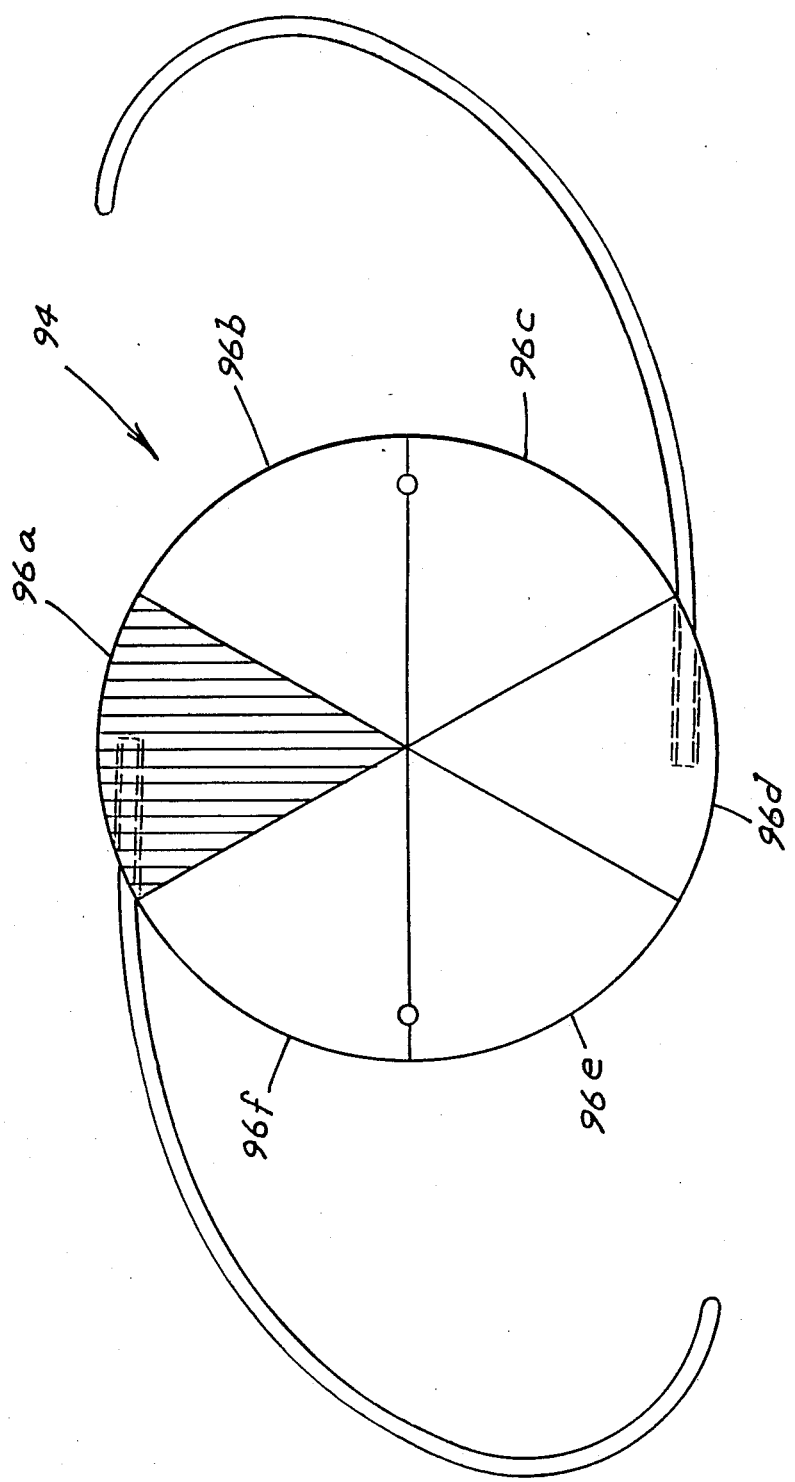
FIG. 7 illustrates a plan view of a radially segmented zone of focus hydrogel lens in which the one lens element is colored and the remaining lens elements are of a common color or clear.

FIG. 7 illustrates a hydrogel lens 94 including lens elements 96a–96f where the lens elements 96a, 96c and 96e have like powers, and lens elements 96b, 96d and 96f have another distinct power in common. Only lens element 96a is colored, such as the color red, and the other elements 96c and 96e of like power are transparent or the same color as elements 96b, 96d and 96f.

Figure 8:
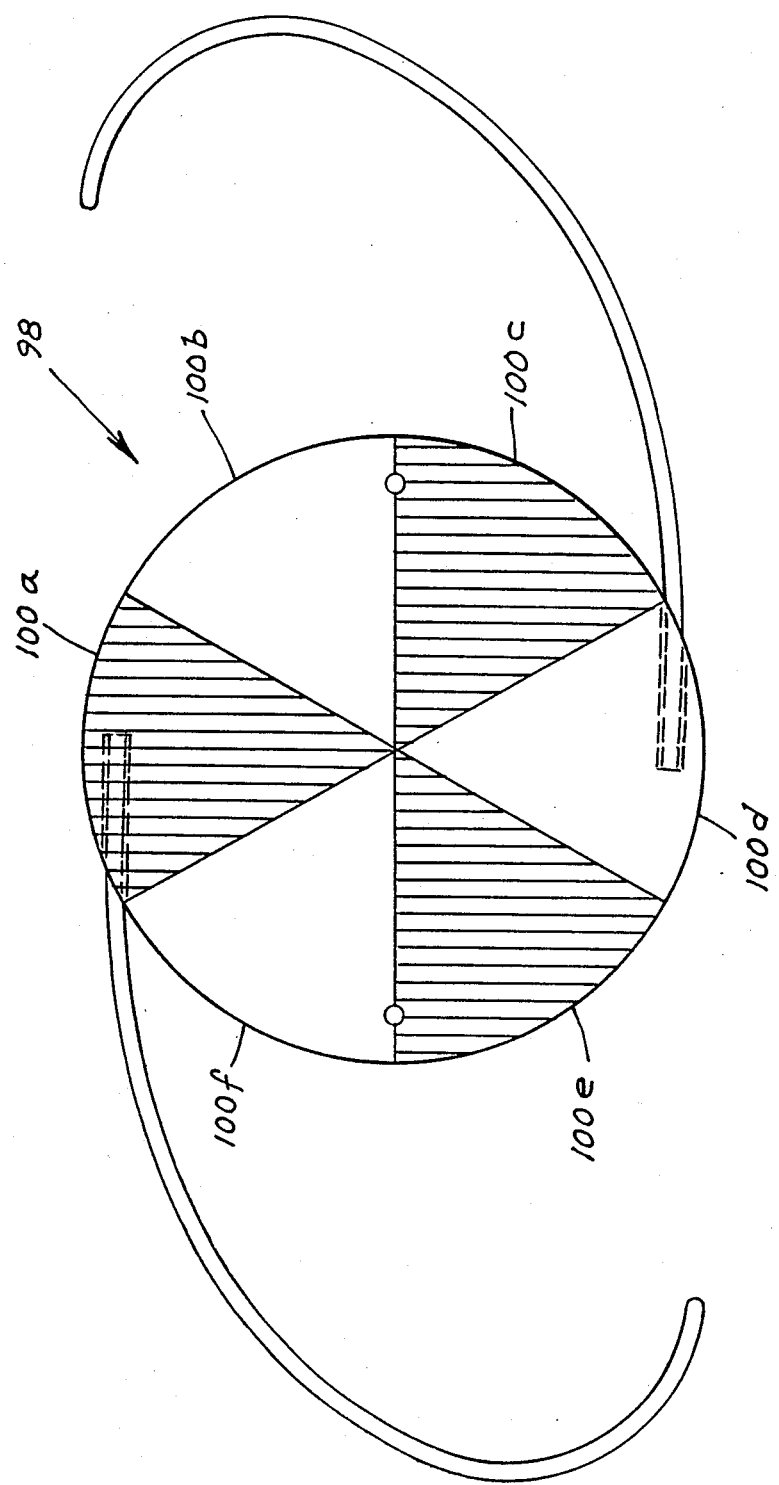
FIG. 8 illustrates a plan view of a radially segmented zone of focus hydrogel lens in which the lens elements are alternating color and clear.

FIG. 8 illustrates a hydrogel lens 98 including lens elements 100a–100f where the lens elements 100a, 100c and 100e have like powers, and the lens elements 100b, 100d and 100f have another distinct power in common. Lens elements 100a, 100c and 100e are colored, such as the color red, and the remaining elements 100b, 100d and 100f are transparent.

Figure 9:
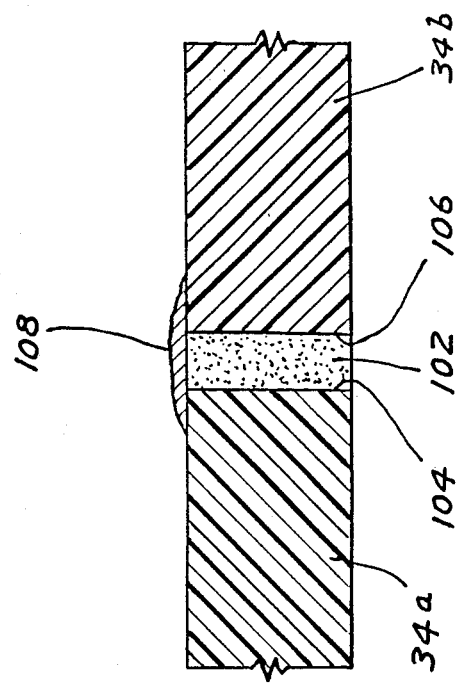
FIG. 9 illustrates a cross-sectional view of the junction between elements illustrating the anti-reflection coating.

FIG. 9 illustrates a sectional view of the hydrogel lens shown in FIG. 1 taken along the line 9—9 of FIG. 1 to show the junction between two elements where the elements are joined subsequent to extrusion. The lens element 34a is joined to element 34b by a layer of transparent adhesive material 102. The material 102 may include an additive to provide antireflective characteristics. Alternatively, a conventional, discrete, antireflective coating may be applied to one or both of the joining surfaces 104 and 106. The use of an anti-reflective coating will generally be beneficial since it reduces the extraneous light reflected from the internal surfaces of the lens. Reflections can also be reduced by applying a thin, highly pigmented opaque layer of material 108 may be applied over the surface area in the region of the junction to masks out the rays which would otherwise produce reflections.

FIGS. 10-15 illustrate some of the element combinations which are contemplated by this invention and are of similar and like construction with regard to surface loops, positioning holes and the like, as previously described in previous figures.

Figure 10:
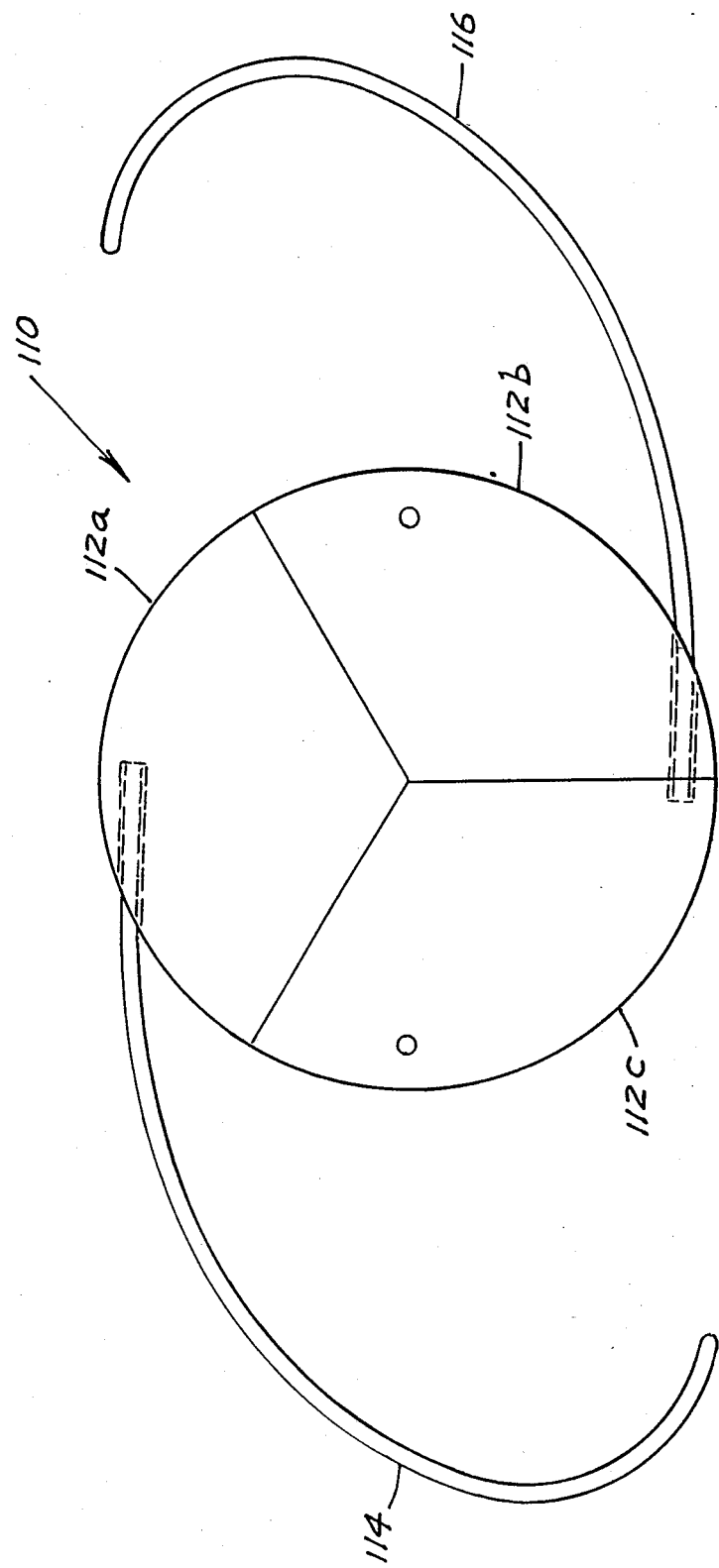
FIG. 10 illustrates a plan view of a radially segmented zone of focus hydrogel lens in which the individual lens elements are of different powers.

FIG. 10 illustrates a hydrogel lens 110 including three lens elements, 112a, 112b and 112c, each having a different power. The point of fixation of the haptics 114 and 116 will be selected to place the desired elements in the proper position for optimum ease of adaptation. For some persons, the optimum position for the most commonly used image, brought to a focus by element 112a, will be the top central portion of the retina. If this is the case, the haptics 114 and 116 will be located to place element 112a in a position to bring its image to the top of the retina.

Figure 11:
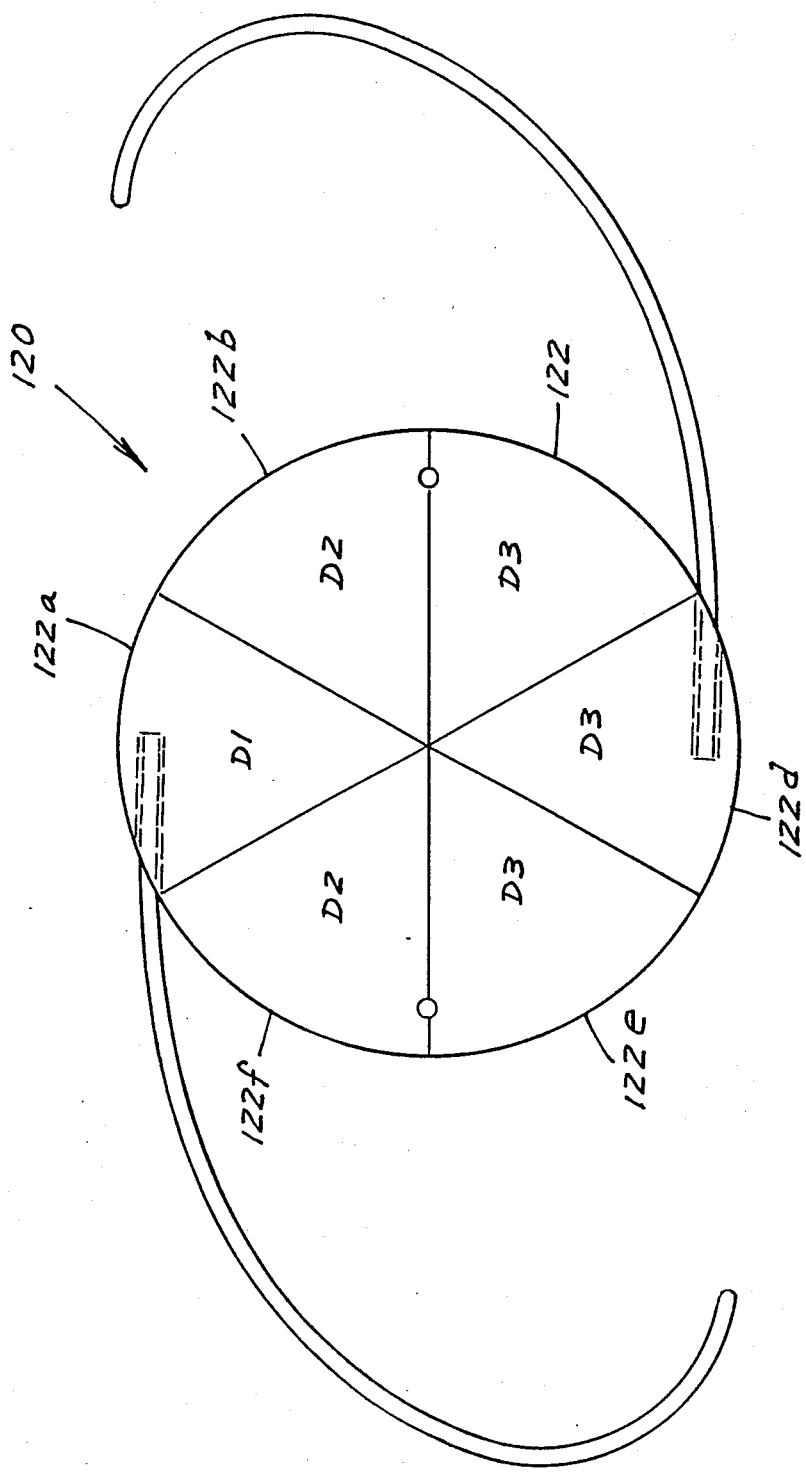
FIG. 11 illustrates a plan view of a radially segmented zone of focus hydrogel lens in which an ever increasing number of powers are grouped in a geometric fashion.

FIG. 11 illustrates a hydrogel lens 120 including six lens elements 122a-122f in which lens element 122a has a power D1, elements 122b and 122f have powers D2, and elements 122c, 122d, and 122e have powers D3.

Figure 12:
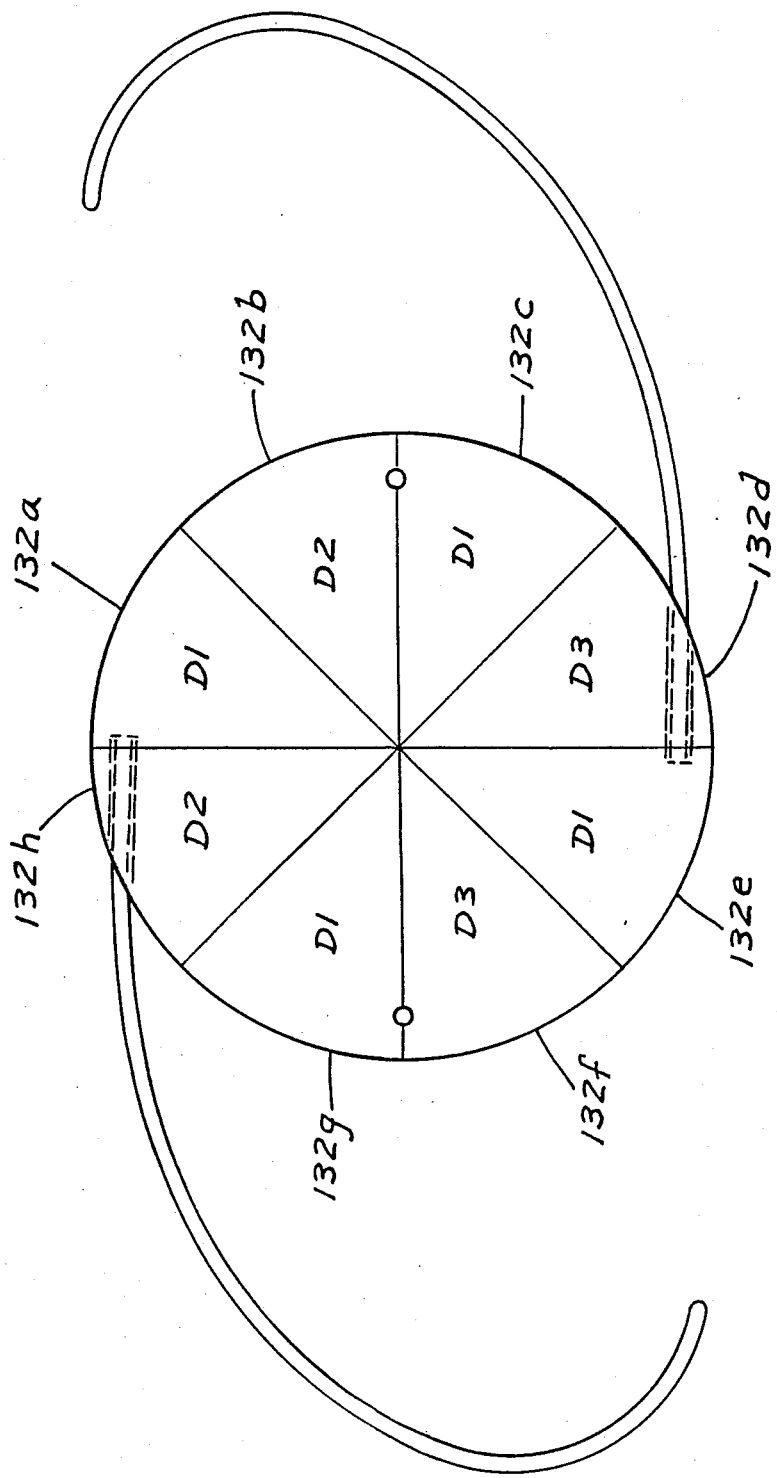
FIG. 12 illustrates a plan view of a radially segmented zone of focus hydrogel lens in which different power lens elements are distributed between opposing alternating lens elements of like power.

FIG. 12 illustrates a hydrogel lens 130 including eight lens elements 132a-132h, wherein elements 132a, 132c, 132e, and 132g have the same power D1, elements 132b and 132h have the same power D2, and the remaining lens elements 132d and 132f have the same power D3.

Figure 13:
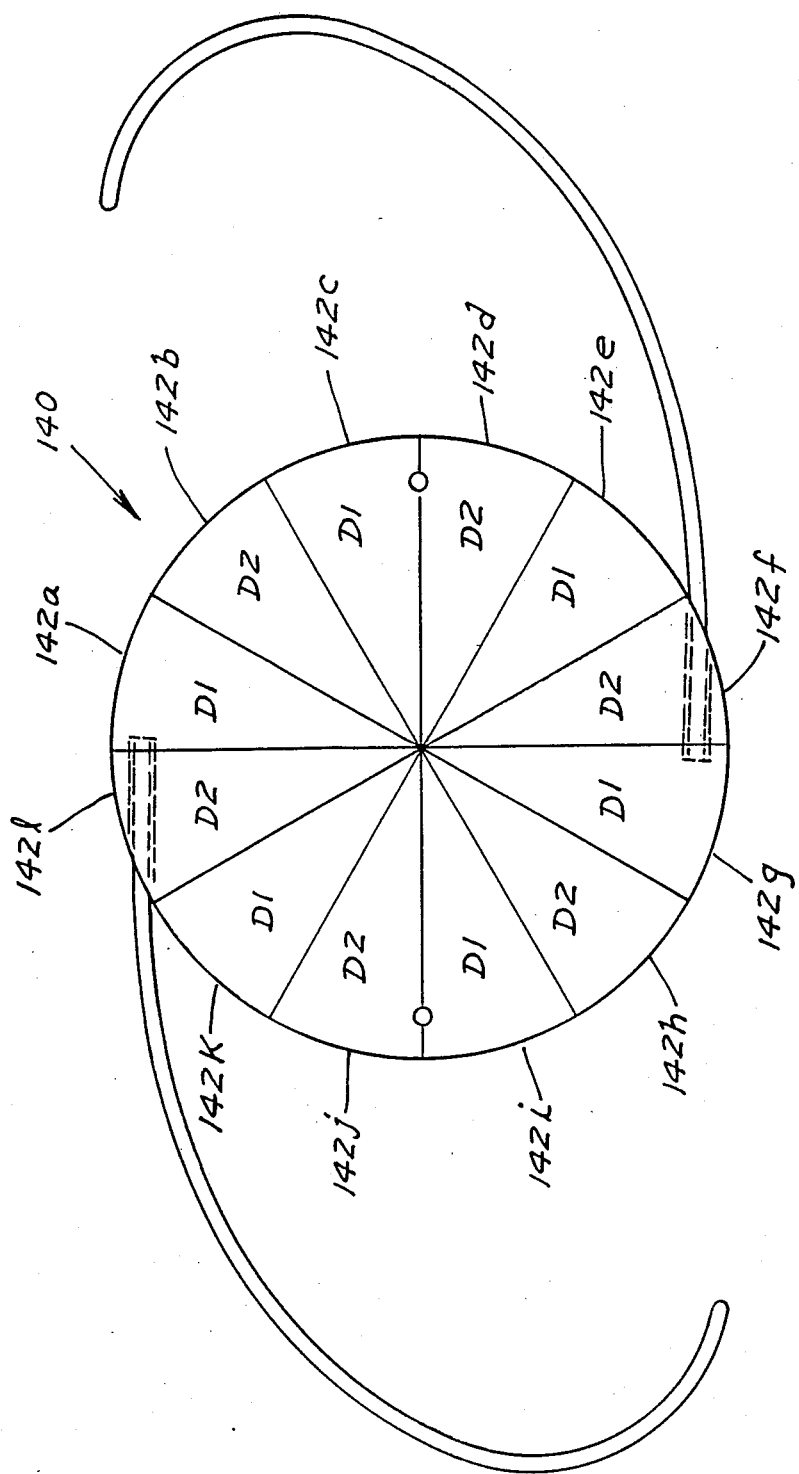
FIG. 13 illustrates a plan View of a radially segmented zone of focus hydrogel lens including 12 alternating power lens elements.

FIG. 13 illustrates a hydrogel lens 140 including 12 lens elements 142a-142l which alternate between powers D1 and D2.

Figure 14:
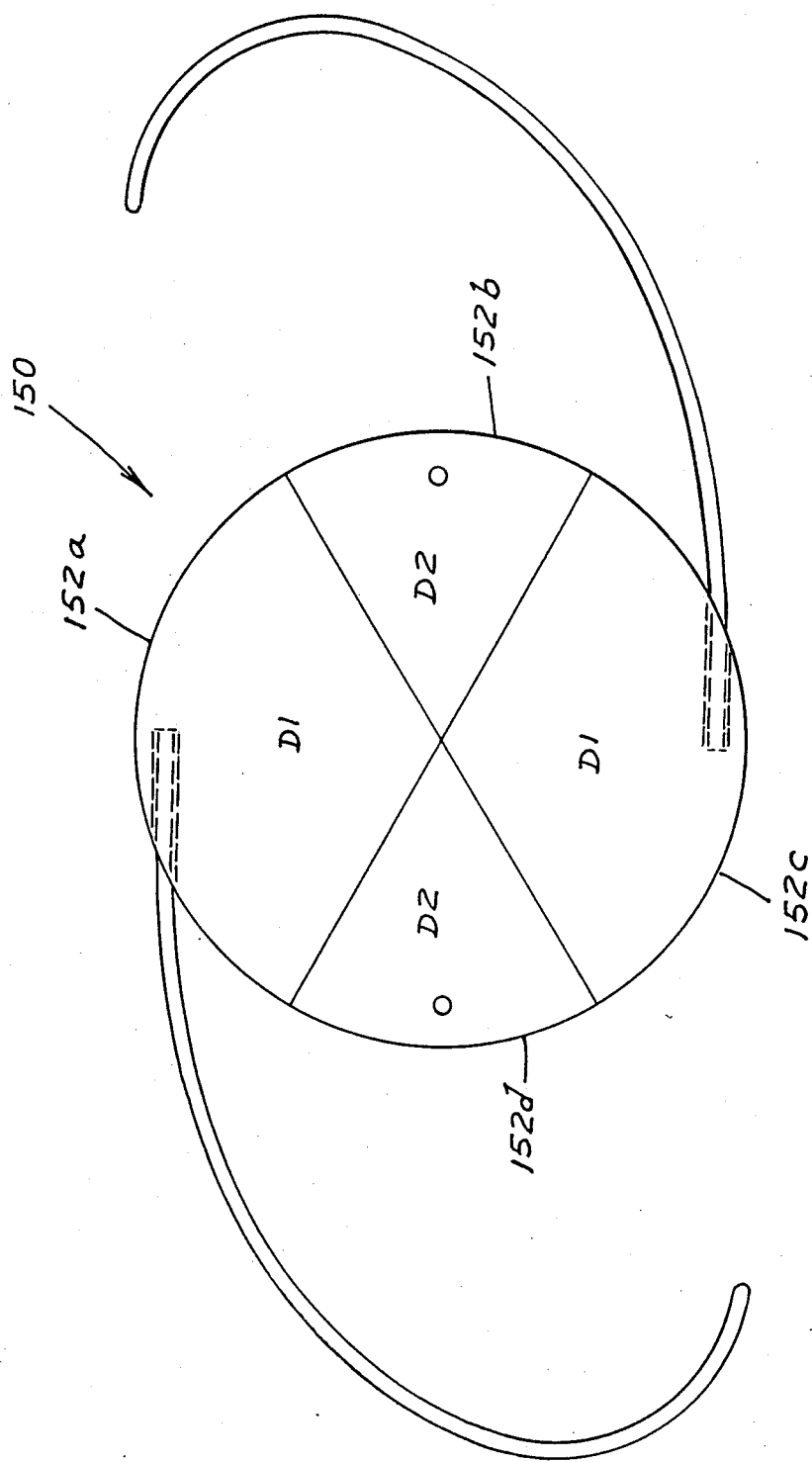
FIG. 14 illustrates a plan view of a radially segmented zone of focus hydrogel lens in which dominant lens elements are arranged along the horizontal axis of the optic.

FIG. 14 illustrates a hydrogel lens 150 including lens elements 152a-152d which differ from those earlier described in that the lens elements are not symmetrical to the adjacent lens element. It can be seen that the elements 152a and 152c, which have like powers D1 make up a larger portion of the lens 150 than do the other two elements 152b and 152c which have like powers D2. This configuration may be used where the use of one power predominates, to facilitate adaptation of the user to the lens.

Figure 15:
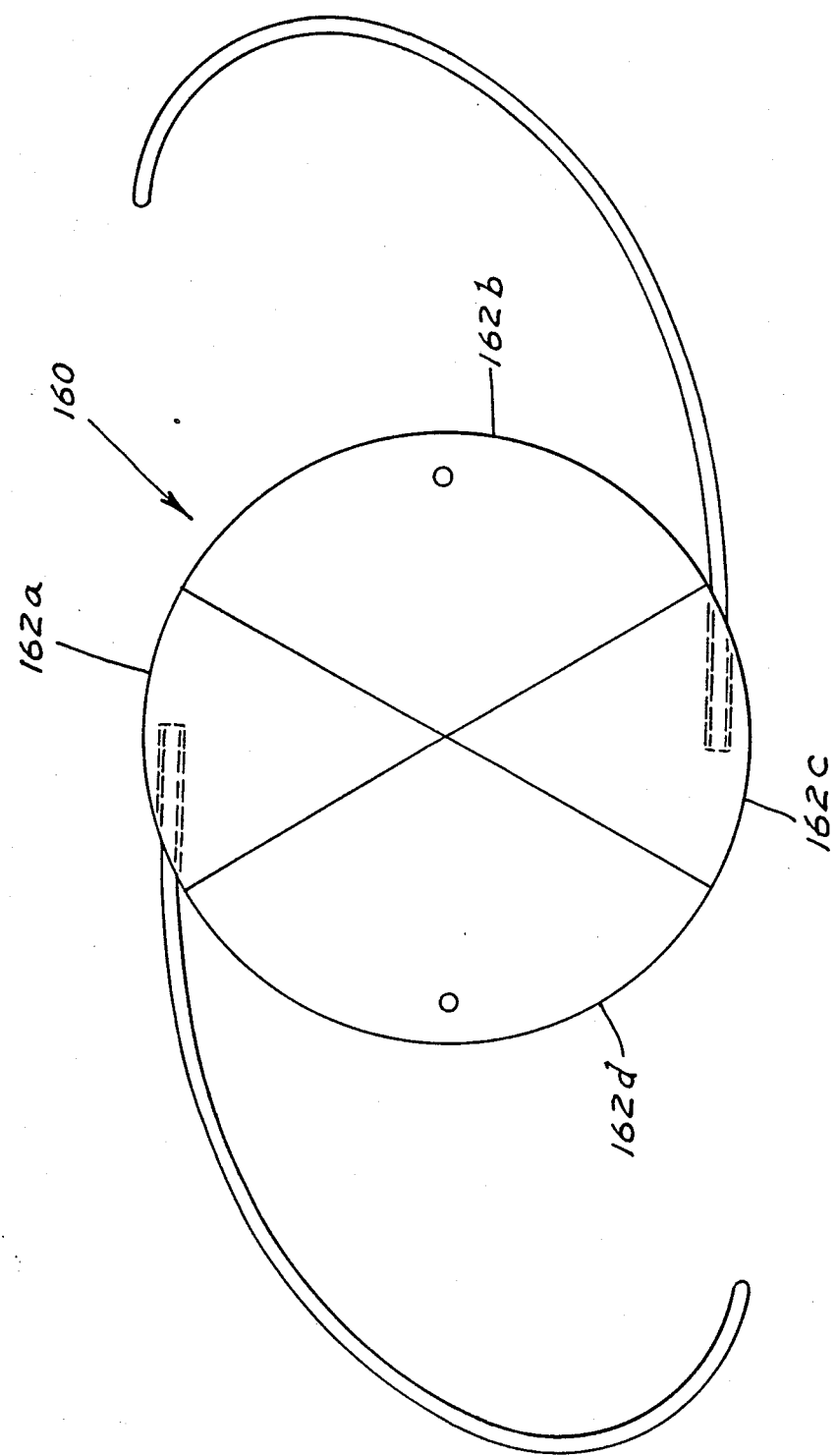
FIG. 15 illustrates a plan view of a radially segmented zone of focus hydrogel lens in which dominant lens elements are arranged along the vertical axis of the optic; and, FIG. 16 illustrates a plan view of paired hydrogel lenses for use in the left and right eyes of a patient.

FIG. 15 illustrates a hydrogel lens 160 including lens elements 162a-162d, which also have nonsymmetrical adjacent lens elements, and in which the predominant elements 162b and 162d are arranged along the horizontal axis, instead of the vertical axis. This is also for the purpose of assisting the user in the adaptation process.

Figure 16:
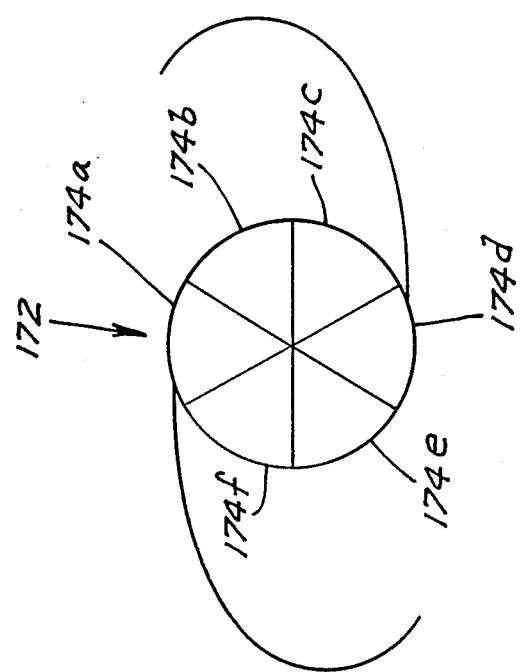
Figure 16:
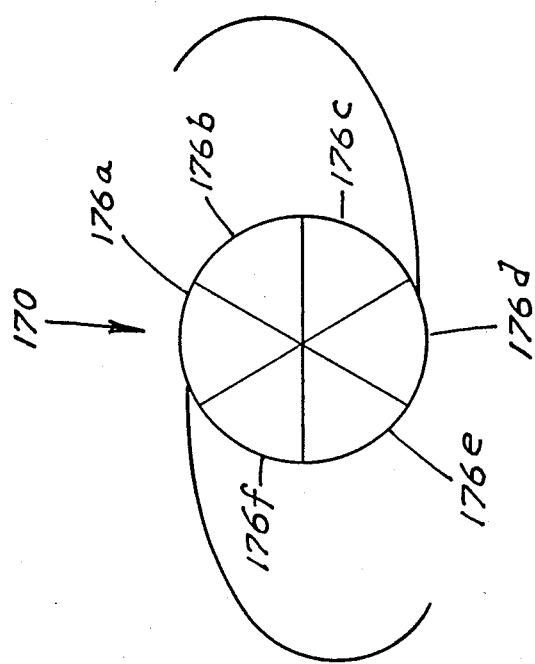

FIG. 16 illustrates two hydrogel lenses 170 and 172 which represent the lenses to be used in the right and left eyes, respectively, of a user. In this embodiment, the lens elements 174a-174f for the left eye have powers respectively corresponding to the powers of lens elements 176a-176f for the right eye. This too, is to facilitate the adaptation process.

MODE OF OPERATION

Reduction of the cost of the lenses would have the effect of increasing the availability of this procedure to those who currently lack the economic means to afford such an operation. This is particularly the case in third world countries where costs are often the overriding consideration in medical care.

There is no question that the technique of using less than the entire retina is usually not as desirable as a system which duplicates the normal lens use of the entire retina. There is a loss of acuity which shows up in reduced resolution and contrast, particularly in low light conditions. In addition, the accommodation of the brain to such a system takes a period of time, and the degree of success in such accommodation varies with individuals.

In the case where a defective natural lens is to be replaced, it is customary to make extensive measurements on the eye prior to the removal of the defective natural lens and its replacement with a fixed focus implantable lens. Such measurements allow the selection of a lens having appropriate power for the individual, and the nominal distance to the object which is desired to be brought into focus on the retina. This approach to the problem has the disadvantage that a wide range of powers must be available to the surgeon. Since each lens is individually fabricated, the economic burden of fabricating a wide variety of powers adds substantially to the cost of lenses. It would be much cheaper to manufacture only a few lenses and use them in all patients. The cost of manufacture would be reduced and inventory requirements would be much less burdensome.

The flexible hydrogel material allows the lens to be folded or rolled up and inserted into the eye through an incision or puncture which is much smaller than required for a conventional, rigid lens. Since the insertion procedure is simplified, the cost of implantation is reduced and the chance for success is enhanced.

Various modifications can be made to the present invention without departing from the apparent scope thereof.

I claim:

1. A zone of focus hydrogel lens for use with an eye comprising:
   a. a plurality of pie-shaped optical hydrogel elements joined at the sides to form a unitary lens structure having a front surface, a rear surface and a circular periphery;
   b. each of said pie-shaped hydrogel elements serving to create an image on a distinct portion of the retina; and
   c. at least two of said hydrogel elements having different powers whereby objects at different distances from the eye are simultaneously brought to a focus on distinct portions of the retina; and
   (d) at least two of said pie-shaped elements are of different colors.

2. A lens according to claim 1 wherein at least two of said pie-shaped elements are of hydrogel materials having different indices of refraction.

3. A lens according to claim 1 wherein at least two of said pie-shaped elements have different surface curvature.

4. A lens according to claim 3 further including a layer of transparent material overlying said front and rear surfaces to provide a smooth exterior.

5. A lens according to claim wherein the boundaries between said pie-shaped elements include an anti-reflective material.

6. A lens according to claim 1 wherein the surface areas of the boundaries between said elements are masked with an opaque material to block passage of rays which would otherwise cause reflections.

7. A lens according to claim 1 wherein said pie-shaped elements are joined with a transparent adhesive material.

8. A lens according to claim 1 wherein said pie-shaped elements are joined during an extrusion process.

9. A lens according to claim 1 wherein adjacent of said pie-shaped elements have different indices of refraction.

10. A lens according to claim 9 comprised of first and second elements having first and second indices of refraction.

11. A lens according to claim 1 comprised of elements each having different indices of refraction.

12. A lens according to claim 11 consisting of three elements.

13. A lens according to claim 11 having at least three elements.

14. A lens according to claim 1 wherein pie-shaped elements of like index of refraction are positioned diametrically opposite in said lens.

15. A lens according to claim 1 wherein said pie-shaped elements providing sharp focus images of near objects are positioned horizontally across said lens.

16. A lens according to claim 1 wherein said pie-shaped elements providing sharp focus images of far objects are positioned vertically across said lens.

17. A lens according to claim 1 wherein said pie-shaped elements providing sharp focus images of near objects are positioned within the lower half of said lens.

18. First and second lenses according to claim 1 for use in left and right eyes wherein like power elements are similarly positioned.

* * * * *